(12) United States Patent
Schwarzberg et al.

(10) Patent No.: US 8,768,727 B2
(45) Date of Patent: *Jul. 1, 2014

(54) METHOD FOR TAILORING STRATEGY MESSAGES FROM AN EXPERT SYSTEM TO ENHANCE SUCCESS WITH MODIFICATIONS TO HEALTH BEHAVIORS

(71) Applicant: Humana Innovations Enterprises, Inc., Louisville, KY (US)

(72) Inventors: Robert Schwarzberg, Boca Raton, FL (US); Marion Zabinski, San Diego, CA (US); Rene Melton, Delray Beach, FL (US); Timothy J. Dion, Parkland, FL (US)

(73) Assignee: Humana Innovations Enterprises, Inc., Lousiville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/915,336

(22) Filed: Jun. 11, 2013

(65) Prior Publication Data

US 2013/0346092 A1 Dec. 26, 2013

Related U.S. Application Data

(63) Continuation of application No. 12/117,190, filed on May 8, 2008, now Pat. No. 8,463,618, which is a continuation-in-part of application No. 11/856,917, filed on Sep. 18, 2007.

(51) Int. Cl.
G06Q 10/00 (2012.01)
G06F 7/00 (2006.01)
A61B 5/00 (2006.01)

(52) U.S. Cl.
USPC .............................................. 705/2; 707/104

(58) Field of Classification Search
USPC .................................................... 705/2
See application file for complete search history.

(56) References Cited

U.S. PATENT DOCUMENTS

| | | | | |
|---|---|---|---|---|
| 5,704,350 A | * | 1/1998 | Williams, III | 600/300 |
| 6,980,999 B1 | * | 12/2005 | Grana | 707/803 |
| 2004/0014014 A1 | * | 1/2004 | Hess | 434/236 |
| 2006/0074279 A1 | * | 4/2006 | Brover | 600/300 |

* cited by examiner

Primary Examiner — Hiep V Nguyen
(74) Attorney, Agent, or Firm — Standley Law Group LLP

(57) ABSTRACT

A system and method for assisting with the maintenance of healthy lifestyle habits by generating tailored strategy messages within an expert system and then pushing those messages to the corresponding individual users of the cellular phones or other portable devices. The system and method allows diet and exercise plans to be tailored to individual users based on their preferences and provides consistent and appropriate strategy messages designed to encourage and motivate users toward successfully maintaining healthy lifestyle habits. Users complete initial assessments which detail individual food and physical activity preferences. The system uses the assessments to generate individualized messages that are pushed to user devices through a system incorporating cellular technologies. Tailored messages are pushed from the computer based expert system to user devices at predetermined times each day.

25 Claims, 27 Drawing Sheets

HOME · WHY Sensei · ARTICLES · RECIPES · HEALTH TOOLS · FAQ · About Sensei · JOIN     MY Sensei.com (login)

Sensei *CHANGING MINDSETS WITH HANDSETS*

Your wellness starts now!

Gender    ○ Male  ⊙ Female

Age       [47]

Weight    [140] Lb

Goal Weight [130] Lb

Height    [5 ▽] Ft [4 ▽] In ( SEND > )

Setting Your Goal Weight

Rome wasn't built in a day, and neither were you! It took a while to gain it, so cut yourself some slack when it's time to lose it. Instead of one BIG goal, set several smaller goals (like 10-15 pounds at a time).

Every pound lost means using 3500 more calories than you take in. Exercise helps burn the calories and gets you to your goal faster.

HOME · WHY Sensei · ARTICLES · RECIPES · HEALTH TOOLS · FAQ · About Sensei · JOIN          MY Sensei.com (login)

Sensei¢HANGING MINDSETS WITH HANDSETS

Join Sensei

Step 2
Account Details

You know the drill. Fill in the blanks.

Pick a username and password.

We'll send you a confirmation by email.

Your credit card will be charged monthly for the term of your Sensei contract. You can cancel at any time by contacting customer support.

Choose a username (8 chars limit) Check username availability
[          ] — 202

Choose a password
[          ]

Confirm your password
[          ]

Email address
[          ]

Security Question
[.........]

Security Answer
[          ]

First Name
[          ] — 204

Last Name
[          ]

Street Address
[          ]

City
[          ]

State
[Choose: ▼]

Zip Code
[          ]

Country
[United States ▼]

FROM FIG-2B1

Birthdate
Month ⌄  Date ⌄  Year ⌄

Phone (xxx-xxxxxxx)
[              ]

Mobile Manufacturer
[        ⌄ ]

Mobile Carrier
[        ⌄ ]

Mobile Number (xxx-xxxxxxx) — 206
[              ]

Mobile Model
[        ⌄ ]

☐ I have read and agree to the Terms of Use.
☐ I have read and agree to the Medical Disclaimer.

(Submit ›)

FIG-2B2 my Sensei HANGING MINDSETS WITH HANDSETS

My Diet Plan         Hello    SIGN OUT | ACCOUNT SETTINGS

Your life needs balance. Your diet needs balance.

Balance, portion control, and increased activity are the core of healthy living. Each plan is a balanced approach to nutrition providing some variations in taste and interests.

All the Sensei's meal plans are healthy, will help you lose weight, and keep it off for a lifetime.

Choose the plan that fits your life
Remember:
Extremes like starvation or deprivation aren't successful or healthy.
Starvation leads to hibernation, slows your metabolism, and slows your weight loss.
Avoiding carbs or fats will only make you crave them more.

---

SENSEI SENSEIBLE/BALANCE PLAN    → CHOOSE

Reduces calories by cutting down fat and sugar
Includes a variety of foods (such as fruits, vegetables, and grain)
Convenience foods easily fit into this plan
Based on 2005 Dietary Guidelines

_MORE..._

SENSEI HEALTHY CARB PLAN    → CHOOSE

A healthier version of popular low carb diets
Includes more lean meat, fish, dairy, nuts
Decreases less healthy carbs and keeps good ones
Limits sweets and baked goods
Convenience foods fit into this diet plan

_MORE..._

SENSEI MEDITERRANEAN PLAN    → CHOOSE

Includes fish, grains, fruits, vegetables, beans and nuts
Major fat is olive oil (monounsaturated) and other unsaturated fats
Some convenience foods may not fit
Some meals can require a little more preparation time for some meals (but we do have Quick & Easy choices too)

_MORE..._

— 208

FIG-2C my sense HANGING MINDSETS WITH HANDSETS

Hello
SIGN OUT | ACCOUNT SETTINGS

Food Filter

↑ SAVE AND CONTINUE — 212

Don't Send Me These!

We promise not to make you eat foods you don't like. Check off the foods that you avoid and we'll keep them out of your menus. Click the box to select a whole food category or click the icon to expand the list and pick certain foods in each group.

☑ – Category fully selected ☑ – Category partially selected
☐ – Category empty

☑ Meat, Poultry and Fish ☑ Beans, Nuts and Seeds

☐ Grains & Soy Products ☐ Fruit

☐ Vegetables ☐ Dairy

☑ Condiments and Dressings

Other Foods or Dishes

Don't see something you're looking for? Type the first letters in a box below and a list of choices will come up. Click the one you want and we'll take that off your menus.

210

FIG-2D my sensei
CHANGING MINDSETS WITH HANDSETS

Hello
SIGN OUT | ACCOUNT SETTINGS

⇧ SAVE AND CONTINUE — 214

Meal Times

Menu's ready!
You'll have 3 meals and 1 snack on the Sensei program. Schedule your meals every 4-5 hours so you don't go too long without eating.

You will hear from us about 1/2 hour before your meals and snacks.

|  | Weekdays | | | Weekends | | |
|---|---|---|---|---|---|---|
| Breakfast | 7 ⌄ | :30 ⌄ | AM ⌄ | 8 ⌄ | :00 ⌄ | AM ⌄ |
| Lunch | 12 ⌄ | :15 ⌄ | PM ⌄ | 12 ⌄ | :00 ⌄ | PM ⌄ |
| Dinner | 6 ⌄ | :30 ⌄ | PM ⌄ | 6 ⌄ | :30 ⌄ | PM ⌄ |
| Snack | 10 ⌄ | :00 ⌄ | PM ⌄ | 10 ⌄ | :00 ⌄ | PM ⌄ |

⇧ SAVE AND CONTINUE

FIG-2E my sensei HANGING MINDSETS WITH HANDSETS

Hello
SIGN OUT | ACCOUNT SETTINGS

My Meal Preparation

Your Meals Your Way
Choose the preparation that best suits you and your lifestyle. You can change your preferences at any time.

Quick & Easy: <10 min prep; soups, sandwiches, salads

Cook at Home: >10 min to fix; grilling, baking, stir frying. Make ahead to save time.

Frozen/Ready to go: frozen meals, prepackaged refrigerated meals, open & eat canned goods, & other portable foods. Great for portion control!

Fast Food: salads, small plain burgers, sandwiches, fruit. *Options are limited and may not follow Sensei diet plan you choose.*

Go Out/Order In: what to order when eating out. Restaurant portions are big-be prepared to take home leftovers or share.

We will automatically send you snacks that are simple to make, so no need to select a preparation for these.

→ SAVE AND CONTINUE

Select Preparation Type (Drag and Drop) — 216

| Quick & Easy | Cook at Home | Frozen/Ready to go | Fast Food | Go Out/Order In |

218

|  | Breakfast | Lunch | Dinner |
|---|---|---|---|
| Weekdays (Mon–Fri) | ⏲ | ▢ | ⏲ |
| Weekends (Sat–Sun) | ⏲ | ⏲ | ⏲ |

→ SAVE AND CONTINUE

FIG-2F

My Behaviors

Changing old habits is HARD! If it was easy, we'd all be fabulously thin! Weight loss isn't just about food, and eating isn't always about hunger. Sensei goes beyond the typical diet plan to focus on eating habits you'd like to change. Habits are behaviors we learn through repetition. To change them requires focus, determination, and repetition of positive behaviors. Think of some challenges you might have, and let's work on them together to build positive habits.

→ SAVE AND CONTINUE

My Biggest challenges in healthy eating is that I have always...(Choose 3) — 220

- ☐ Eating when I am stressed
- ☑ Eating in front of the television or when I use the computer
- ☐ Snacking late at night
- ☐ Being an emotional eater (happy and/or sad)
- ☐ Eating when I am bored or don't have things to do
- ☑ Eating too many sweets/snacks at work
- ☑ Being tempted to eat food when it is just there, even if I am not hungry
- ☐

Of your challenges, pick one to work on first — 222

- ⦿ Being tempted to eat food when it is just there, even if I am not hungry
- ○ Eating too many sweets/snacks at work
- ○ Eating in front of the television or when I use the computer

FROM FIG-2G1

Here are a list of strategies to help you. Pick 1 that fits your lifestyle best

○ Reach for some sugar-free gum to keep your mouth busy without calories
○ Keep snacks in hard to reach places like the top shelf of the cupboard, behind the paper towels
○ Boredom=snacking. Get busy
○ Out of sight, out of mind. Keep hard to resist foods out of the house! If you have to snack, at least let it be healthy.
○ Exercise! Activity is the healthiest way to occupy your time
○ Call a friend and spend time catching up
○ Don't leave food on display-that can trigger an urge.
○ Keep a sugar-free drink handy, staying hydrated can help manage an urge to munch
○ Distract your attention by doing a chore-if at home, clean 1 room in the house
● Head outside for a walk to clear your head and refocus on something other than food

224

FIG-2G2 my senseï̈HANGING MINDSETS WITH HANDSETS

Hello
SIGN OUT | ACCOUNT SETTINGS

My Activity

⇧ SAVE AND CONTINUE

Time to get moving!
Exercise is a crucial part of the weight loss equation. Regular activity gives you faster results, more energy, and makes you feel great. Tell us about your current fitness level so we can create a customized activity program for you.

I would describe my current activity level as: — 226

○ Not active: I sit at my desk or at home most of the day.
○ Light activity: I try to do some activities a few times a week (e.g., walking at an easy pace, household chores, etc.) I do not do regular exercise but am on my feet most of the day.
● Moderate activity: I am regularly active during the week by walking briskly, or playing sports like tennis or basketball.
○ Vigorous activity: I regularly perform vigorous exercise by running, cycling, or swimming laps, etc. at a high intensity.

I have been exercising (e.g. walking briskly, jogging, cycling, etc.) _____ days per week for at least 20 minutes. — 228

○ 0
● 1-2
○ 3 or more

Do you smoke? — 230

○ Yes
● No

Jane Smith, we're ready to help you reach your weight goal of 130lbs.

Nutrition

Your diet plan: SENSEI SENSEIBLE/ BALANCE PLAN

Your food filter:
> Meat, Poultry and Fish
> Nuts & Seeds (all)
> Olives

Your meal preparations:

| | Breakfast | Lunch | Dinner |
|---|---|---|---|
| Weekdays | | | |
| Weekends | | | |

Fitness — 242

Exercise is one of the most powerful things you can do for your health. It's a no-brainer; regular activity along with a healthy diet is the best way to lose weight and maintain it for the long haul.

It's great that you're already doing some exercise. Based on what you told us, we've put together the following exercise program to help you improve your fitness level:

Cardiovascular activities:

| Bicycling | Walking |
|---|---|

Days of activity:

Over time, we will help you increase your duration and frequency so you are doing more.

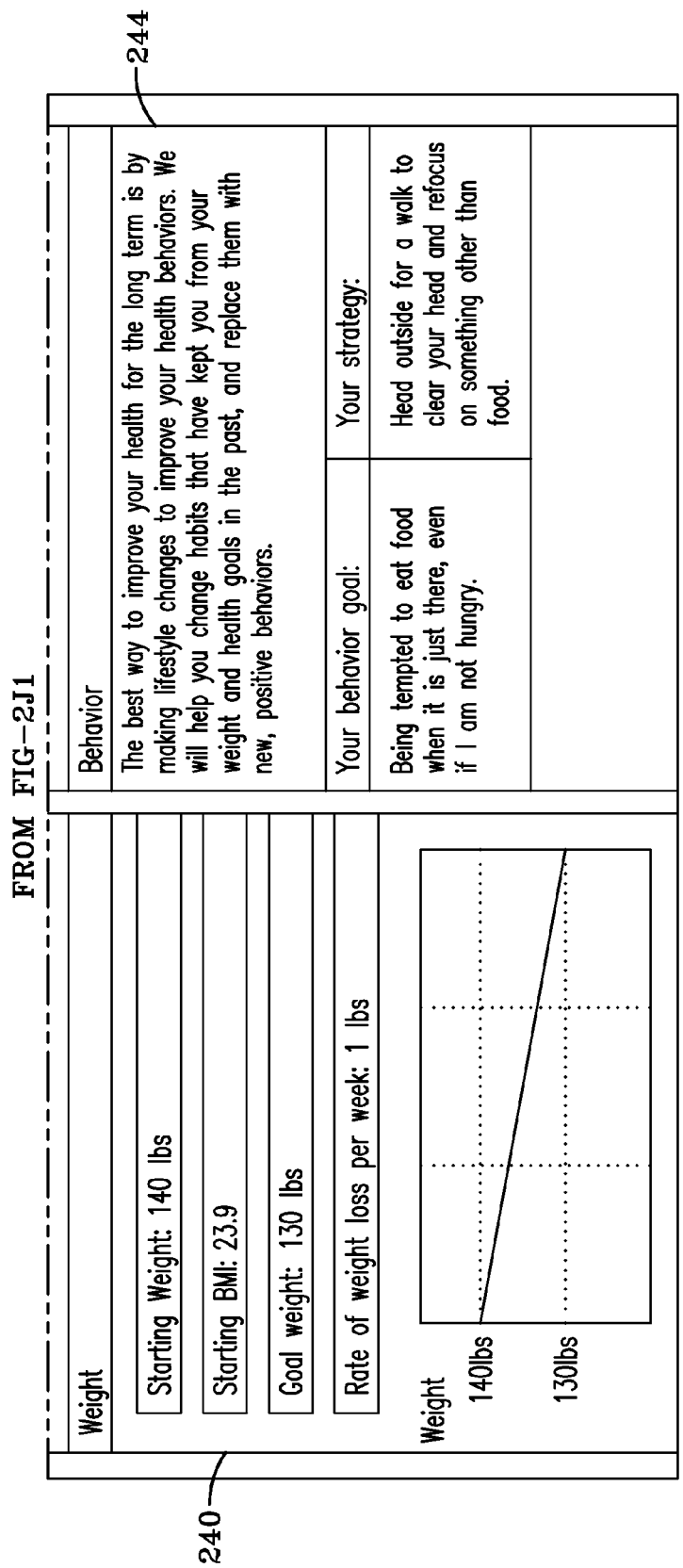
FIG-2J2 my sense CHANGING MINDSETS WITH HANDSETS

Hello
SIGN OUT | ACCOUNT SETTINGS

| MY DAY | MY PLAN | MY LIFESTYLE AND GOALS | SUPPORT GROUP | RECIPES |

◁ Tue, Jan 5th △

| DIFFERENT DATE | PRINT | SHOPPING LIST | REPORT A CHANGE IN MY PLAN |
|---|---|---|---|
| 07:00 AM | Weight | | |
| 07:30 AM | Breakfast: English muffin with cheese & fruit | | |
| 08:00 AM | Walking | | |
| 12:15 PM | Lunch: Lean Meal Cheese ravioli | | |
| 06:30 PM | Dinner: Tortellini & veg | | |

Slice mushroom & saute in margarine w/ garlic, salt, pepper, rosemary,...make it tasty. Warm sauce in microwave. Cook tortellini as directed, drain & top w/ sauce. You may serve garlic mushrooms as a side dish or add them to the sauce.

— 246

My Goal Weight — 250

1 2 3 4 5 6 7 8 9 10
Weeks

Hi Jane,
your goal is to:
Reduce eating when not hungry.

FROM FIG-2K1

Click on any ingredient for info and substitutions

1 Cup Cheese tortellini (332kcal)

0.5 Cup Spaghetti sauce cnd (60kcal)

1 Each Portabella mushroom, fresh (27kcal)

1 Teaspoon Margarine red. cal (50cal/Tbsp) (17kcal)

Total meal calories: 436 calories     CHANGE THIS MEAL

| 10:00 PM | Snack: Papaya |

Total day calories: 1200 calories

248

Today's Tip

Put a picture on the fridge of something that motivates you... your children, a thinner you, friends...you decide.

From Sensei Library

Dieting Does Not Equal Deprivation

Do you feel deprived every time you start a diet? That might be one of the reasons that diets don't last!

Check our blog: Sensei Thoughts.

Here is where the Sensei team will share thoughts on what's happening in the world of health and wellness.

New In My Groups

FIG-2K2 mysensei
CHANGING MINDSETS WITH HANDSETS

Hello
SIGN OUT | ACCOUNT SETTINGS

| MY DAY | MY PLAN | MY LIFESTYLE AND GOALS | SUPPORT GROUP | RECIPES |

MY DIET | MY FITNESS | MY FOOD PREFERENCES

My Diet Plan

| My Plan | CHANGE PLAN |
|---|---|
| SENSEI SENSEIBLE/ BALANCE PLAN | |

| | MON | TUE | WED | THU | FRI | SAT | SUN | PRINT MY DIET PLAN |
|---|---|---|---|---|---|---|---|---|
| 07:30 AM | | | Breakfast: English muffin with cheese and fruit | | | | | |
| 12:15 PM | | | Lunch: Lean meal Cheese ravioli | | | | | |
| 06:30 PM | | | Dinner: Tortellini & veg | | | | | |
| 10:00 PM | | | Snack: Papaya | | | | | |

— 252

Your Guidelines

Reduces calories by cutting down fat and sugar.
Includes a variety of foods (such as fruits, vegetables, grain).
Convenience foods easily fit into this plan.
Based on 2005 Dietary Guidelines.

FIG-2L

METHOD FOR TAILORING STRATEGY MESSAGES FROM AN EXPERT SYSTEM TO ENHANCE SUCCESS WITH MODIFICATIONS TO HEALTH BEHAVIORS

CROSS-REFERENCE TO RELATED APPLICATIONS

This application is a continuation of U.S. patent application Ser. No. 12/117,190 filed May 8, 2008, titled METHOD FOR TAILORING STRATEGY MESSAGES FROM AN EXPERT SYSTEM TO ENHANCE SUCCESS WITH MODIFICATIONS TO HEALTH BEHAVIORS, now U.S. Pat. No. 8,463,618, issued Jun. 11, 2013 and a continuation-in-part of U.S. patent application Ser. No. 11/856,917 filed Sep. 18, 2007, titled SYSTEM AND METHOD FOR REWARDING USERS FOR CHANGES IN HEALTH BEHAVIORS, which is incorporated herein by reference.

TECHNICAL FIELD

The present invention relates to a system and method for assisting with the maintenance of healthy lifestyle habits. More particularly, the present invention is system and method for assisting with the maintenance of desirable diet, exercise, and/or other health behaviors and habits through the sending of various tailored messages from an expert system using at least one portable device coupled to a data network.

BACKGROUND OF THE INVENTION

Many people are affected by a variety of health problems including obesity, diabetes, high blood pressure, and elevated cholesterol levels which can be linked to poor habits in diet, exercise, and the like. Although people are generally aware that controlling diet, exercise, and similar lifestyle habits is the easiest way to become or stay healthy, getting them to adopt and maintain these habits is a difficult task. Many people do not have access to information or to systems or methods that can effectively assist them in these challenging endeavors.

There are many well-known diet and exercise regimes. When using these known regimes, however, individuals must determine what to eat and when to eat as well as calculate the calories they have consumed (e.g., by determining the calorie count of all foods or adding points that are tied to the calorie counts of certain foods) and they must keep an exercise record and determine the caloric impact of their exercise on their overall regime. Another problem with current diet and exercise regimes is that they restrict severely the types of food individuals can consume or the types of activities in which they are guided to participate. This lack of variety causes individuals to become frustrated with their regimes and to give up before they have experienced their desired results.

There are a few known methods and systems for assisting individuals with the maintenance of healthy lifestyle habits, but these methods and systems are expensive and often inaccessible to most people. For example, a highly effective method for assisting individuals in developing and maintaining healthy lifestyle habits is found through the use of coaching. Research has shown that individuals are more successful in the difficult endeavor of changing their habits and maintaining new, healthier ones when they are coached throughout the process. Coaching keeps individuals motivated, provides positive reinforcement, and introduces a narrowly-tailored plan for each individual participant. However, obtaining a reliable human coach is difficult and often prohibitively expensive such that relatively few individuals are actually able to use one. In addition to purchasing the services of a human coach, it has been shown that the services of a personal chef, who is trained in preparing healthy meals, and/or those of a nutritionist, who is able to develop a personalized diet plan, are successful methods for an individual to be assisted in maintaining healthy lifestyle habits, but these methods are also expensive and thus inaccessible to many.

In an attempt to make the services of coaches, nutritionists, personal chefs, and the like accessible to those who could not afford them otherwise, many books have been written and/or home videos produced that focus on disseminating the type of expert information these individuals typically offer their clients. Unfortunately, those who invest in these books and/or videos are noticeably less likely to maintain the healthy lifestyle habits they aim to encourage than those who invest in the actual expert services. The mass marketed materials are aimed at a wide audience and cannot meet the needs of each individual purchaser. The difference that actual health and fitness experts can provide is the ability to provide their clients with appropriate plans and strategy messages with modifications tailored to the individual thereby reducing or eliminating the various barriers to success.

In light of these foregoing problems with known systems and methods, there is a need for a generally affordable and accessible system and method that assists in the maintenance of healthy lifestyle habits by providing individual users with a diet and exercise regime specifically tailored around their personal preferences so that they are not restricted to the point that they become frustrated thus discontinuing their practice of the regime's healthy habits. Additionally, there is a need for a system and method that assists individual users in determining what foods they should be eating, when they should be eating, and/or in what activities they should be participating. The system and method should account for an individual user's preferences, including preferences for meal preparation. Furthermore, the system and method should provide individual users with personalized guidance and strategy similar to that which can be provided by health and fitness experts in order to maximize the probability that individuals will successfully maintain healthy lifestyle habits.

SUMMARY OF THE INVENTIVE CONCEPT

The present invention is a system and method for assisting with the maintenance of healthy lifestyle habits by generating tailored strategy messages within an expert system and then pushing those messages to the corresponding individual users. The system and method utilizes modern technologies, such as the cellular phone or other portable device, to facilitate the pushing of the tailored messages from the system's computer-based expert system to the individual users.

The system and method allows diet and exercise plans to be tailored to individual users based on their preferences and provides consistent and appropriate strategy messages designed to encourage and motivate users toward successfully maintaining healthy lifestyle habits. Several embodiments illustrate ways in which an individual user can utilize personalized instruction from a trained expert in the dieting field, without having to meet with them personally and without having to pay the prohibitively expensive fees that are typically associated with personalized instruction. Exemplary embodiments allow the individual user to utilize portable technology, such as cell phones, handheld computing devices, and personal digital assistants (PDA), so that the user has constant access to their personalized instruction.

In one embodiment, individual users complete initial assessments which detail each individual's food and physical activity preferences. These assessments can then be used to compile profiles for each individual that are stored in a database. The system and method uses the profile information in the database to generate individualized messages that can then be pushed to individual users through a system incorporating cellular technologies. In one embodiment of the system, tailored messages are pushed from the computer based expert system to an individual user's cell phone at predetermined times each day. In one such embodiment, a message generated by the computer-based expert system provides an individual user with a healthy suggestion for his or her next meal based on the type of food he or she indicated to have preferred when completing the initial assessment. In another embodiment of the system, a message generated by the computer-based expert system provides an individual user with a healthy suggestion of a physical activity that should be performed based on the type of physical activity he or she indicated to have preferred in the initial assessment.

The system and method can be interactive and an individual user can respond to suggestive messages they have received by either accepting or rejecting the suggestions with a reply message. In one embodiment, the computer-based expert system analyzes reply messages generated by individual users. For example, if an individual user indicates a desire to reject a given suggestion in a reply message, the computer-based expert system detects that desire through analysis and generates a new message for the user that contains a different suggestion designed to replace that which the user had previously rejected. Likewise, if an individual user indicates in a reply message a desire to accept a given suggestion, the computer-based expert system detects that desire through analysis of the reply.

In one embodiment, the system and method tracks the actions taken and the progress made by individual users. For example, if an individual user desires to lose weight the system monitors the food the individual consumes and the physical activities the individual performs. The system updates the information at the database as a result of the monitoring. The updated information in the database helps to ensure that the system sends messages that are appropriate for each individual user as their habits and/or preferences change. The system can additionally track an individual's actual progress and generate messages praising users when they get closer to their goals. The system can also generate messages intended to motivate individual users.

The system and method pushes tailored messages from a computer-based expert system to the portable or cellular devices of individual users and receives responses to help the system's users find healthy food and drinks that they like. Additionally, the system and method uses positive reinforcements and other messages to encourage and motivate individual users to maintain the healthy lifestyle habits they desire. The present invention is both affordable and accessible because it is operated via applications to prevalent and relatively inexpensive modern technologies. The system and method addresses problems inherent in the prior art and makes the key to good health accessible in an original and novel way.

BRIEF DESCRIPTION OF THE DRAWINGS

FIGS. 2A, 2B1, 2B2, 2C, 2D, 2E, 2F, 2G1, 2G2, 2H, 2I, 2J1, 2J2, 2K1, 2K2, and 2L are screen shots for completing a user profile and specifying preferences according to an example embodiment;

DETAILED DESCRIPTION

One exemplary embodiment is a "smart system" designed to encourage and motivate users towards successfully maintaining healthy lifestyle habits by pushing tailored messages from a computer based expert system to individual users via cellular technologies. The system incorporates the personal preferences of individual users in regard to diet, exercise, and other similar habits in conjunction with personal information such as age, weight, gender, and desired results as well as behavioral challenges in order to generate tailored messages to assist individual users with the adoption and maintenance of healthy lifestyle habits.

Figure 1:
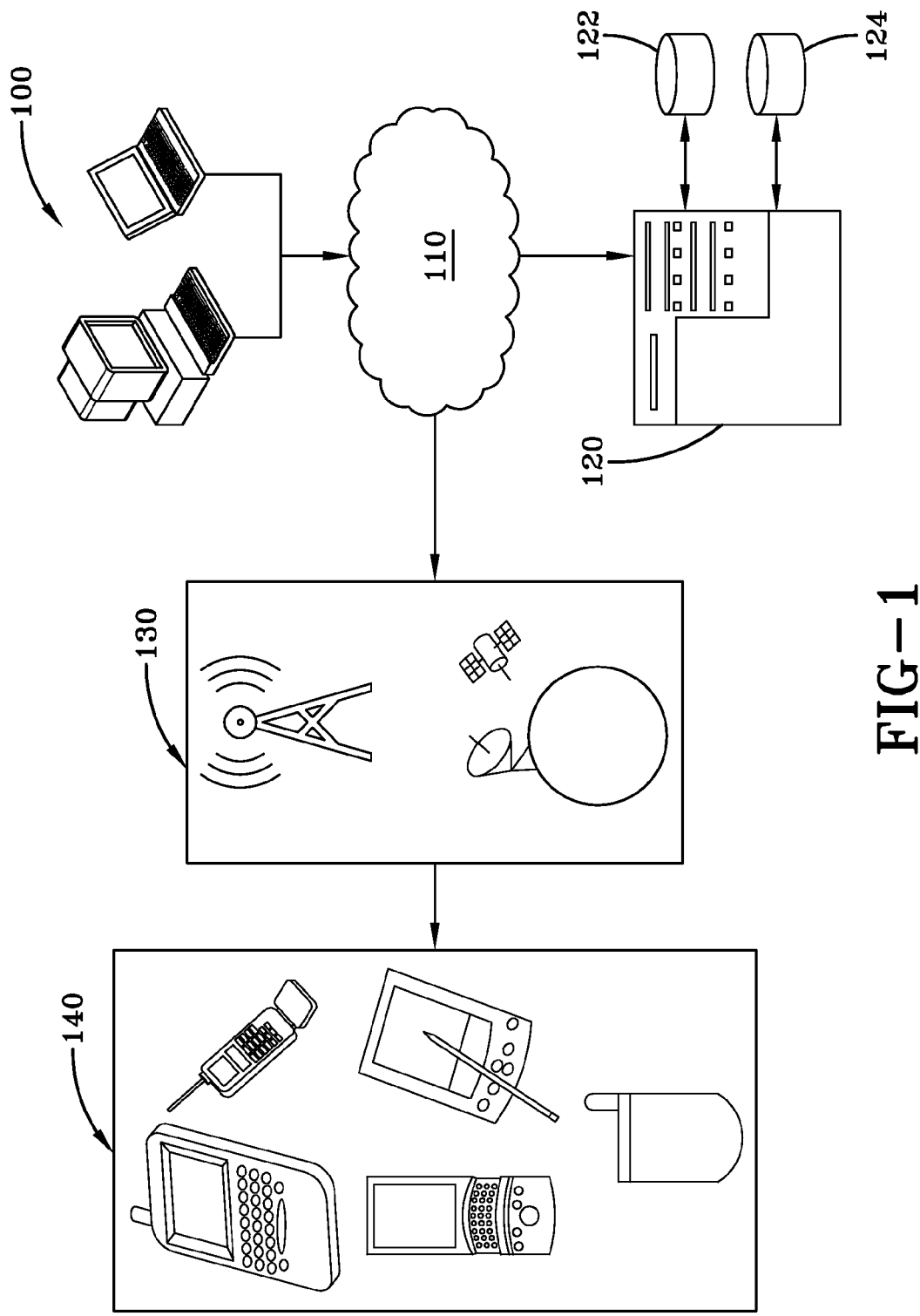
FIG. 1 illustrates the physical structure of a system according to an example embodiment.

FIG. 1 shows one embodiment of the physical structure of the system. Each of the connections mentioned here permit data to flow in both directions. A laptop or desktop personal computer 100 is connected to the server 120 through the internet 110. The user may connect to a website to create an account and enter personal information and preferences for creating a profile. The server 120 is connected to one or more databases 122, 124 comprising user data, nutrition provider data (nutritional data related to meals offered by a plurality of meal providers), diet, and exercise data, message data, progress data, compliance data, restaurant, shopping, and entertainment establishment data, reward data, and other data as may be required to provide the features and functionality of the present invention. The server 120 is connected to communication networks 130 (comprising various data transmitters and receivers) through the internet 110. The various data transmitters and receivers of the communication networks 130 facilitate communications with the user's portable technology 140 which includes cellular or mobile phones, personal digital assistants, or any other portable device capable of sending and receiving communications through the communication networks 130 and displaying them for a user. An expert system at the server uses the individual's account information, including information about the individual's mobile phone, to tailor and send to the individual messages to reinforce and motivate healthy habits.

In an example embodiment, the expert system is constructed using the J2EE programming language in conjunction with a SQL based database (like Microsoft SQL Server or Oracle DB). AJAX, Active X, and Java components may also be used to handle various aspects of the system. The mobile component of the overall system is constructed using the J2ME programming language sending wireless requests to the expert system over common carrier communication protocols. Communication between the mobile component and the expert system is constructed using XML language structures.

Referring to FIGS. 2A-2L, screen shots for completing a user profile, specifying diet and exercise preferences, and identifying health behavioral challenges in an enrollment process according to an example embodiment are shown. The user provides contact and background information, specifies a weight goal, specifies preferences related to diet and exercise, and identifies personal behavioral challenges. The user's profile data and specified goal and diet and exercise preferences are considered by the expert system to tailor messages intended to reinforce and motivate behaviors that are important in helping the user reach the specified goal. The user accesses a website to navigate through the screens and provide data and information that allows the system to build a profile for the user comprising diet and exercise preferences as well as behavioral challenges.

Referring to FIG. 2A, a screen for specifying physical characteristics and a weight goal is shown. The user specifies a sex, age, weight, and height and a goal weight 200. This information is saved in the user's profile and used to determine the user's progress toward the goal. The expert system generates tailored messages that help the user to progress toward the specified goal.

Referring to FIG. 2B1, an account screen for an example embodiment is shown. First, the user specifies a username, password, and email address to create an account 202. Next, the user provides contact information 204. Referring to FIG. 2B2, the user also provides information about his or her mobile phone or other portable device so that messages from the expert system can be pushed to the portable device 206.

Referring to FIG. 2C, a diet plan screen for an example embodiment is shown. The user specifies the type of diet plan he or she would like to follow. In an example embodiment, the user may select from one of three diet plans 208. A first plan is a balanced plan which emphasizes a diet of reduced calories as well as reduced fat and sugar. A second plan is a healthy carbohydrate plan that emphasizes a diet of lean meats, fish, dairy, and nuts. A third plan is a Mediterranean plan that emphasizes a diet of fish, grains, fruits, vegetables, beans, and nuts.

Referring to FIG. 2D, a food preference screen for an example embodiment is shown. The user selects a food category and identifies the foods in each category that he or she does not like or wants to avoid 210. In an example embodiment, the categories include: 1) meats, poultry, and fish; 2) beans, nuts, and seeds; 3) grains and soy products; 4) fruit; 5) vegetables; 6) dairy; and 7) condiments and dressings. Within each category, the user can select from a list the foods he or she does not want to eat. Alternatively, an entire category of food can be selected. Finally, if the user does not find a particular food on any list within a category, the specific food can be entered in a text box 212. As the user types, choices matching the entered text are presented. Foods identified in the text boxes as well as foods selected from the category lists are not included in any menu or meal suggestions that are provided to the user.

Referring to FIG. 2E, a meal times screen according to an example embodiment is shown. The user specifies a time of day for eating breakfast, lunch, and dinner as well as a snack 214. The user specifies two sets of meal times, one for weekdays and one for weekends. Referring to FIG. 2F, a meal preparation preference screen according to an example embodiment is shown. On this screen, the user specifies preferences related to meal preparation options 216. Using a drag and drop feature, the user specifies meal preparation preferences for breakfast, lunch, and dinner on weekdays and weekends 218. In an example embodiment, the meal preparation options are: 1) quick and easy (fewer than 10 minutes to prepare); 2) cook at home (more than 10 minutes to prepare); 3) frozen or ready to eat; 4) fast food; or 5) order from restaurant. The meal preparation preferences provide additional data for the expert system to consider when generating messages to the user related to meal options.

Referring to FIG. 2G1, a behavior challenges screen according to an example embodiment is shown. The screen presents common challenges to a healthy lifestyle 220 and allows the user to select the ones that are applicable. The user is also asked to identify the challenge he or she would like to overcome first (a priority challenge) 222. Referring to FIG. 2G2, the screen presents a list of strategies for overcoming common challenges 224. The user is asked to select a strategy that is appropriate for the user's lifestyle. The user's selections related to applicable challenges, a priority challenge, and a challenge strategy are considered by the expert system in generating tailored messages.

Figure 2I:
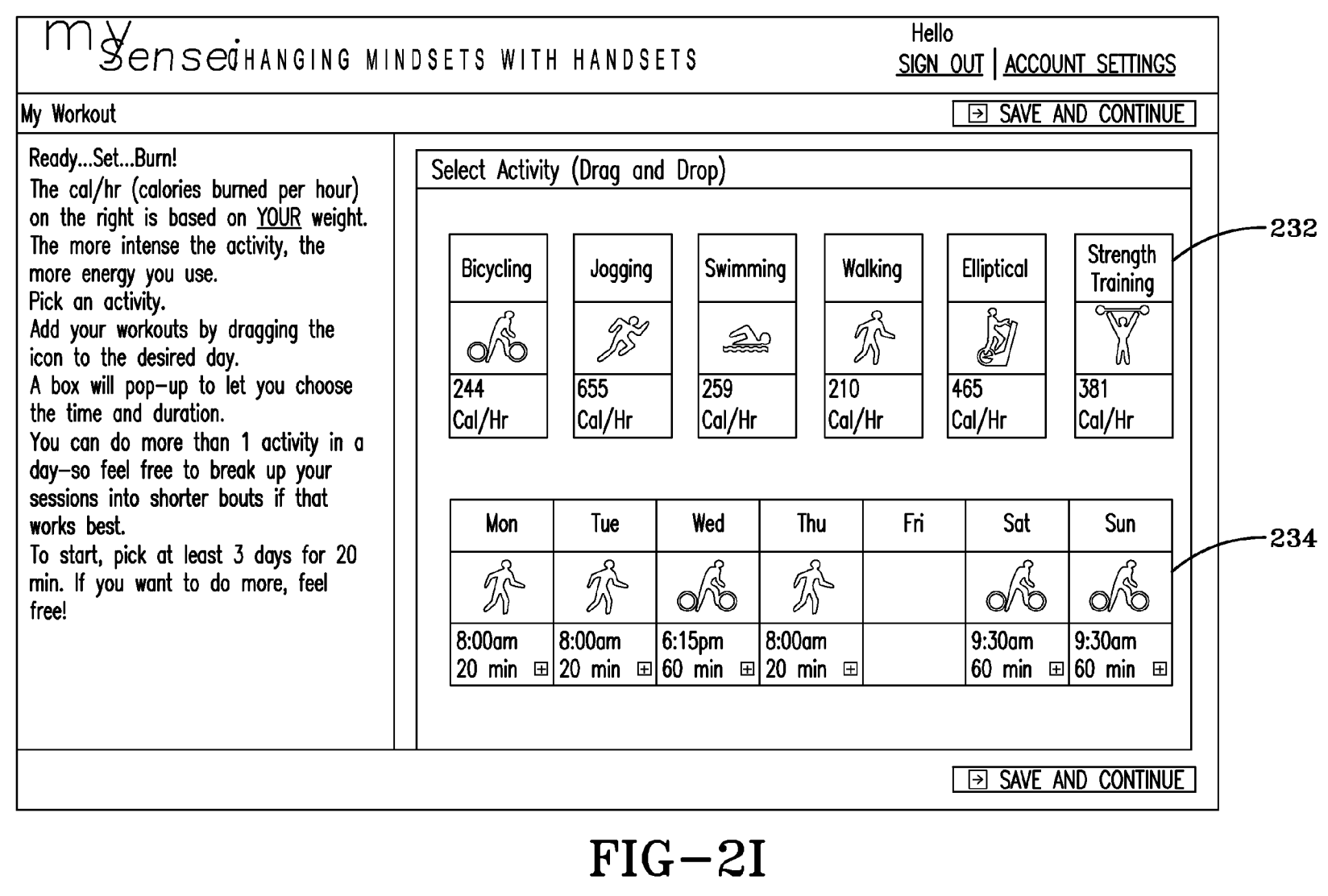

Referring to FIG. 2H, an activity screen according to an example embodiment is shown. The user provides information about his or her current activity level 226 and exercise frequency 228. In addition, the user indicates whether he or she smokes 230. The user's selections related to current activity level, exercise frequency, and smoking are considered by the expert system in generating tailored messages. Referring to FIG. 2I, a workout screen according to an example embodiment is shown. Using a drag and drop feature, the user identifies preferred physical activities 232 and specifies times for performing the physical activities on a weekly basis 234. The preferences related to physical activities and times are considered by the expert system in generating tailored messages.

Referring to FIG. 2J1, a profile overview screen according to an example embodiment is shown. The screen presents information regarding the data and preferences specified by the user while completing the profile data entry screens. A nutrition section comprises the user's selections related to a diet plan and specific food preferences 236 as well as meal preparation preferences 238. Referring to FIG. 2J2, a weight section comprises the user's personal data related to current weight and body mass index as well as goal weight and proposed rate of weight loss per week 240. Referring to FIG. 2J1, a fitness section comprises the user's selections related to physical activity preferences 242. Referring to FIG. 2J2, a behavior section comprises information about the user's priority challenge and preferred strategy from overcoming the challenges he or she specified previously 244.

Referring to FIG. 2K1, a daily plan screen according to an example embodiment is shown. The daily plan screen presents a complete schedule of activities and meal suggestions based on the personal data and preferences specified by the user previously 246. In the example schedule, the user takes a weight reading at 7:00 AM, eats the suggested breakfast at 7:30 AM, completes the suggested activity at 8:00 AM, and eats the suggested lunch and dinner at the specified times. Referring to FIG. 2K2, the daily plan screen also presents food substitution suggestions in the event the user does not want to follow the initial meal suggestion 248. The user can select any ingredient in the specified meal suggestion and select a substitution. The ability to substitute ingredients in a specified meal allows the user change the meal only slightly or to change the entire meal to meet his or her preferences at mealtime. Referring to FIG. 2L, a diet plan screen according to an example embodiment is shown. At this screen, the user can review the weekly meal suggestions 252 and complete any substitutions prior to receiving the meal suggestions on at the mobile phone or other portable device.

Figure 3A:
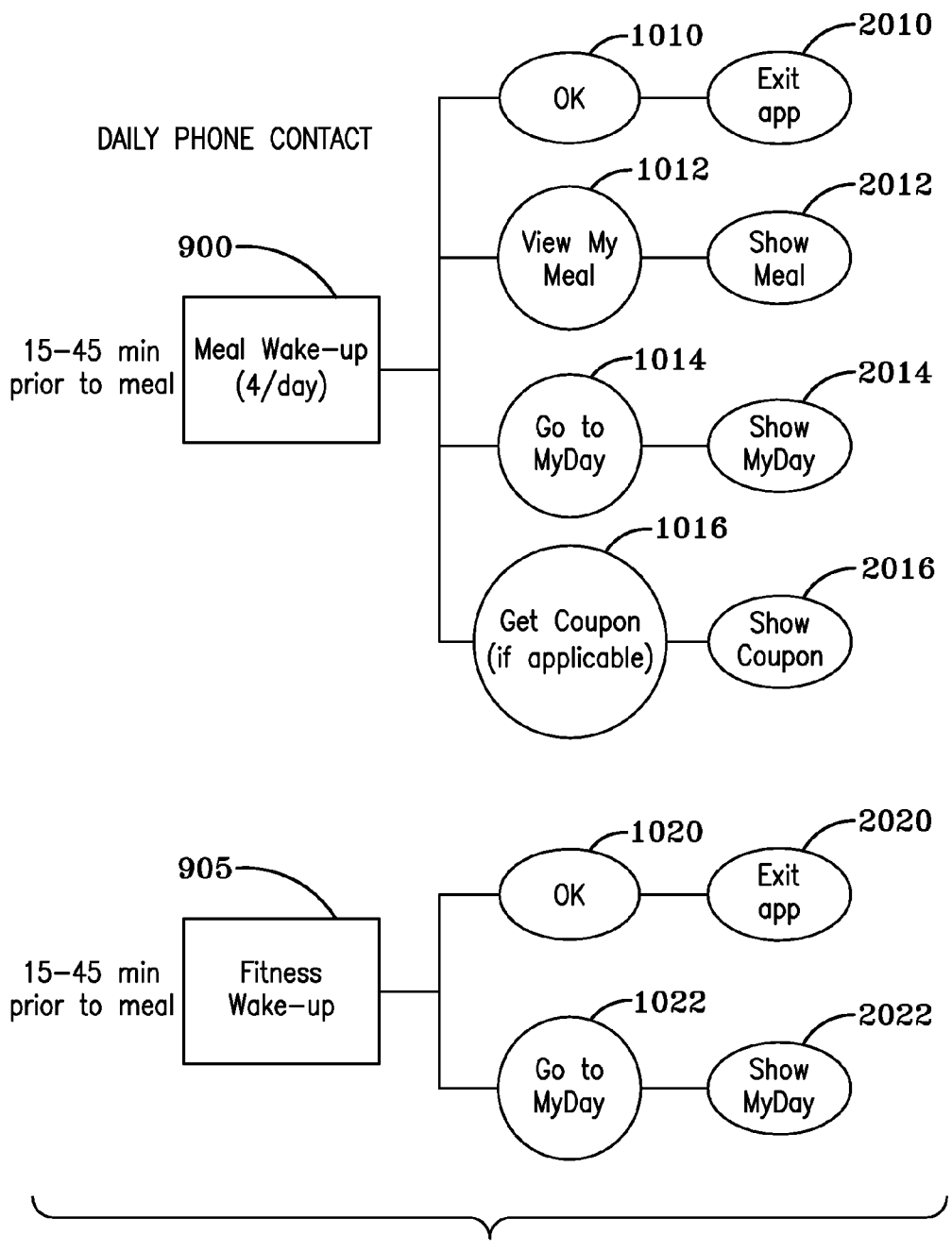
FIGS. 3A-3C are a flowchart illustrating daily phone contacts and weekly phone contacts according to an example embodiment.
Figure 3B:
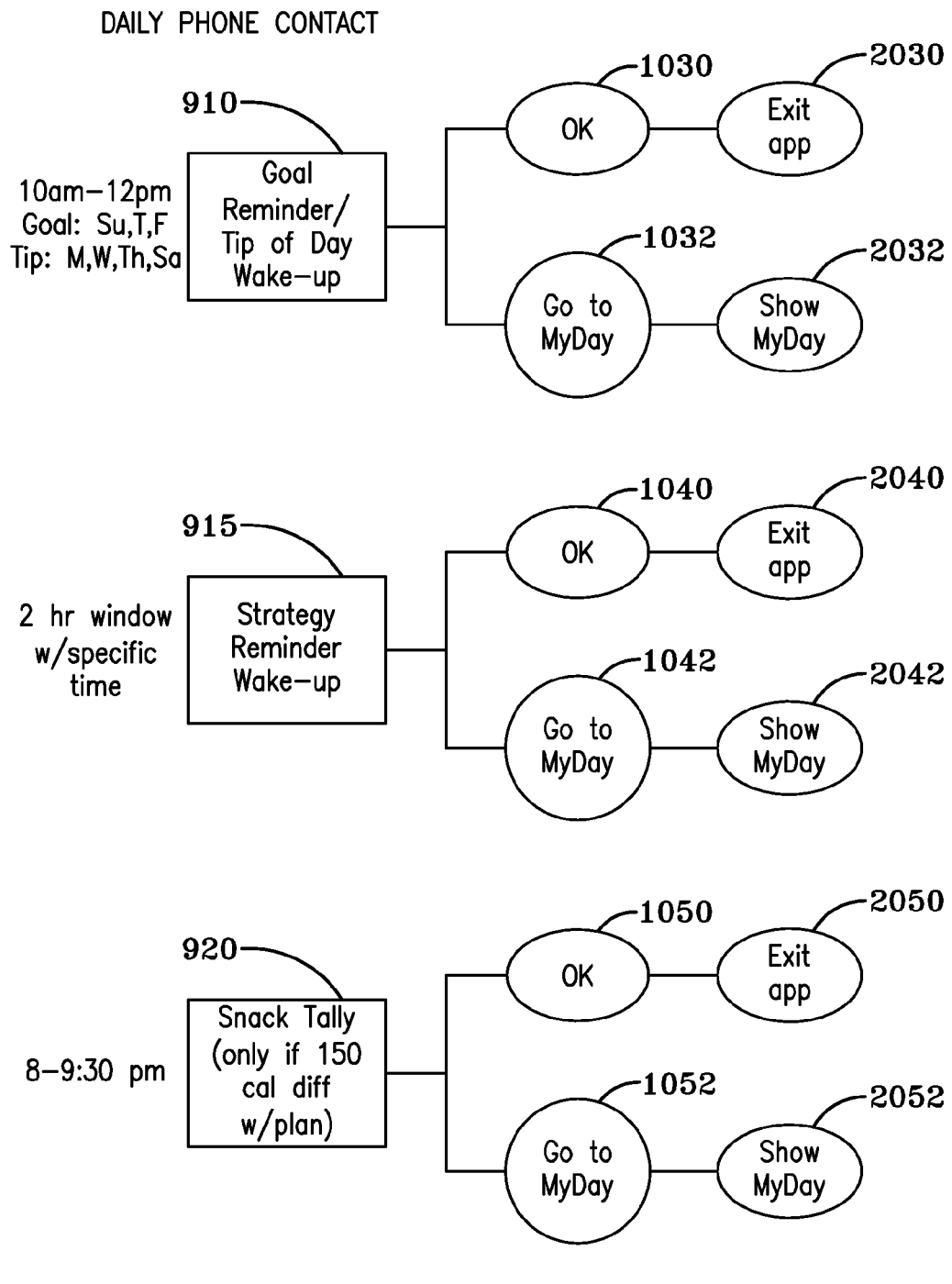
Figure 3C:
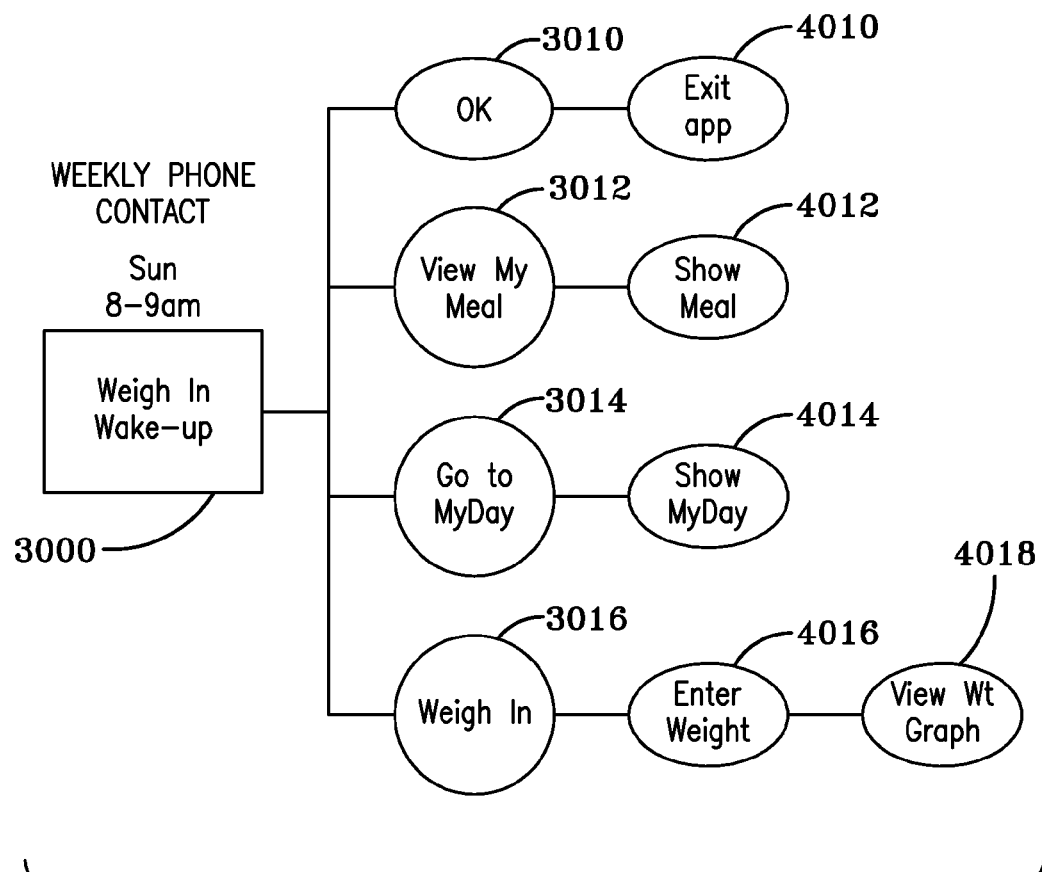

FIGS. 3A-3C are a flow chart illustrating daily phone contacts and weekly phone contacts according to an example embodiment. Referring to FIGS. 3A and 3B, a variety of tailored daily messages 900 through 920 are sent daily to an individual user. The tailored messages 900 through 920 are pushed from the computer based expert system to an individual user's cell phone. Once a tailored daily message 900 through 920 is received by an individual user, the individual user is presented with a variety of responses 1010 through 1052. The individual user is able to select one of a variety of responses 1010 through 1052 and send the selected response on to the computer based expert system. The computer based expert system detects the response sent by the individual user and responds with one of a variety of reply messages 2010 through 2052.

In an exemplary embodiment of the system and method daily messages 900 through 920 in five categories are sent from the computer based expert system to the cellular communications device of an individual user. These daily messages 900 through 920 include a plurality of "Meal Wake-up" messages 900, one or more "Fitness Wake-up" messages 905, a "Goal Reminder/Tip of the Day Wake-up" message 910, a "Strategy Reminder Wake-up" message, and a "Snack Tally" message 920. An individual user specifies times for eating meals and exercising. The daily tailored messages 900 through 920 are programmed to arrive at the cellular communications device within a certain time range based on the user's specified times for various activities.

To understand how the tailored messages of the system and method are used to assist an individual user in the maintenance of healthy lifestyle habits consider a "Meal Wake-up" message 900. An individual user receives a meal wake-up message 900 any time from 15 to 45 minutes before the user's preferred time for each daily meal. Once a meal wake-up message 900 is received by an individual user, the individual user is presented with a variety of responses 1010 through 1016. The individual user may respond with an "OK" response 1010, a "View Meal" response 1012, a "Go to MyDay" response 1014, or a "Get Coupon" response 1016. Fewer or more response options may be provided based on the activity for which the message is sent. Depending on which one of a variety of responses 1010 through 1016 an individual user selects, the computer based expert system responds by sending one of a variety of reply messages 2010 through 2016 to the individual user's cellular communications device. The computer based expert system may send an "Exit Application" reply 2010 (not seen by the user), a "Show Meal" reply 2012, a "Show MyDay" reply 2014, or a "Show Coupon" reply. For example, if an individual user selects a "View Meal" response 1012 after viewing his or her meal wake-up message 900, the computer based expert system detects this selection and replies with a "Show Meal" response 2012.

The computer based expert system accesses a database that contains the personal preference data of individual users and uses the personal preference data to formulate tailored messages which are then pushed on to the corresponding individual users. For example, the database might contain information concerning the meals an individual user prefers to eat and more specifically what types of ingredients the individual would like to be included in his or her diet. Additionally, the personal preference information within the database could include the types of physical activity in which an individual user enjoys participating. The system and method can be configured such that after an individual user receives a "meal wake-up" message 900 and responds with a "View My Meal" response 1012, the computer based expert system replies with a "Show Meal" reply 2012 containing a meal suggestion incorporating the types of food the individual user has previously indicated, through his or her personal preference data, that he or she prefers.

Similarly, the system and method can be configured such that after an individual user receives a "fitness wake-up" message 905 and responds with a "Go to MyDay" response 1022, the computer based expert system replies with a "Show MyDay" reply 2022 containing a physical activity suggestion incorporating the types of activities the individual user has previously indicated, through his or her personal preference data, that he or she prefers. In one exemplary embodiment of the system and method an individual user can incorporate physical fitness information into his or her personal information stored within the database of a computer based expert system. This ensures that when the individual user receives a "Show MyDay" reply 2022 it contains a suggestion for the individual user to participate in a preferred physical activity.

Referring to FIG. 3C, in addition to daily phone contacts, weekly phone contacts 3000 may be sent to individual users. An example weekly phone contact 3000 is a weigh-in wake-up message as shown in FIG. 3C. It could also be a grocery shopping wake-up message that directs the user to purchase food for the week or a motivational wake-up message that encourages the user to continue healthy habits. As shown in FIG. 3, a weekly phone contact 3000 could be followed by a variety of user responses 3010 through 3016. When an individual user selects a response 3010 through 3016, the computer based expert system detects which response was selected and responds with one of a variety of reply messages 4010 through 4014. The weekly phone contact 3000 weigh-in wake-up message reminds the user to get weighed and then respond to the message with an "Enter Weight" response 4016. The computer based expert system then generates a "Weight Graph" reply message 4018 containing a graph showing the individual user's weight loss progress.

Figure 4A:
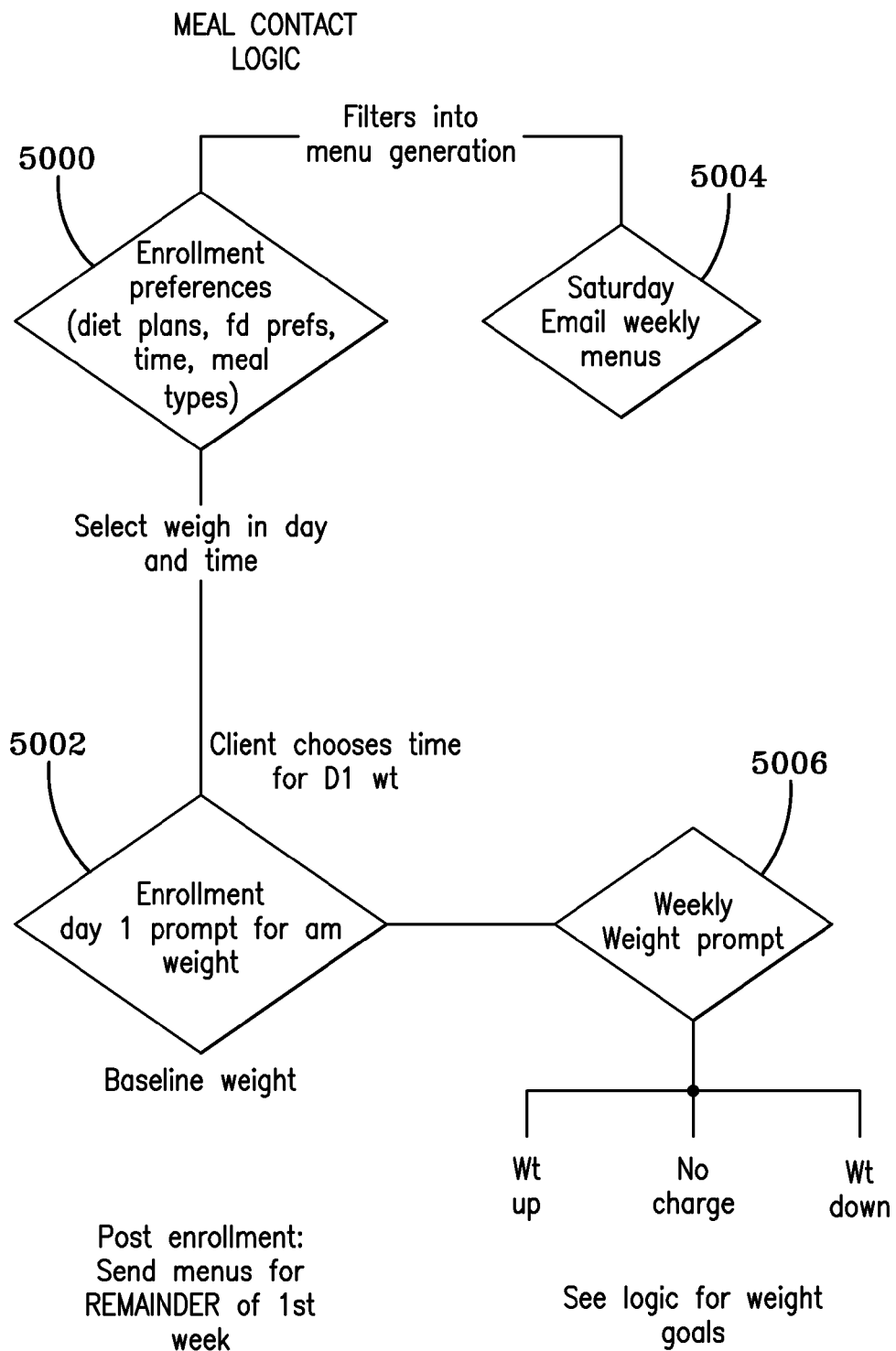
FIGS. 4A-4C illustrate meal contact logic according to an example embodiment.
Figure 4B:
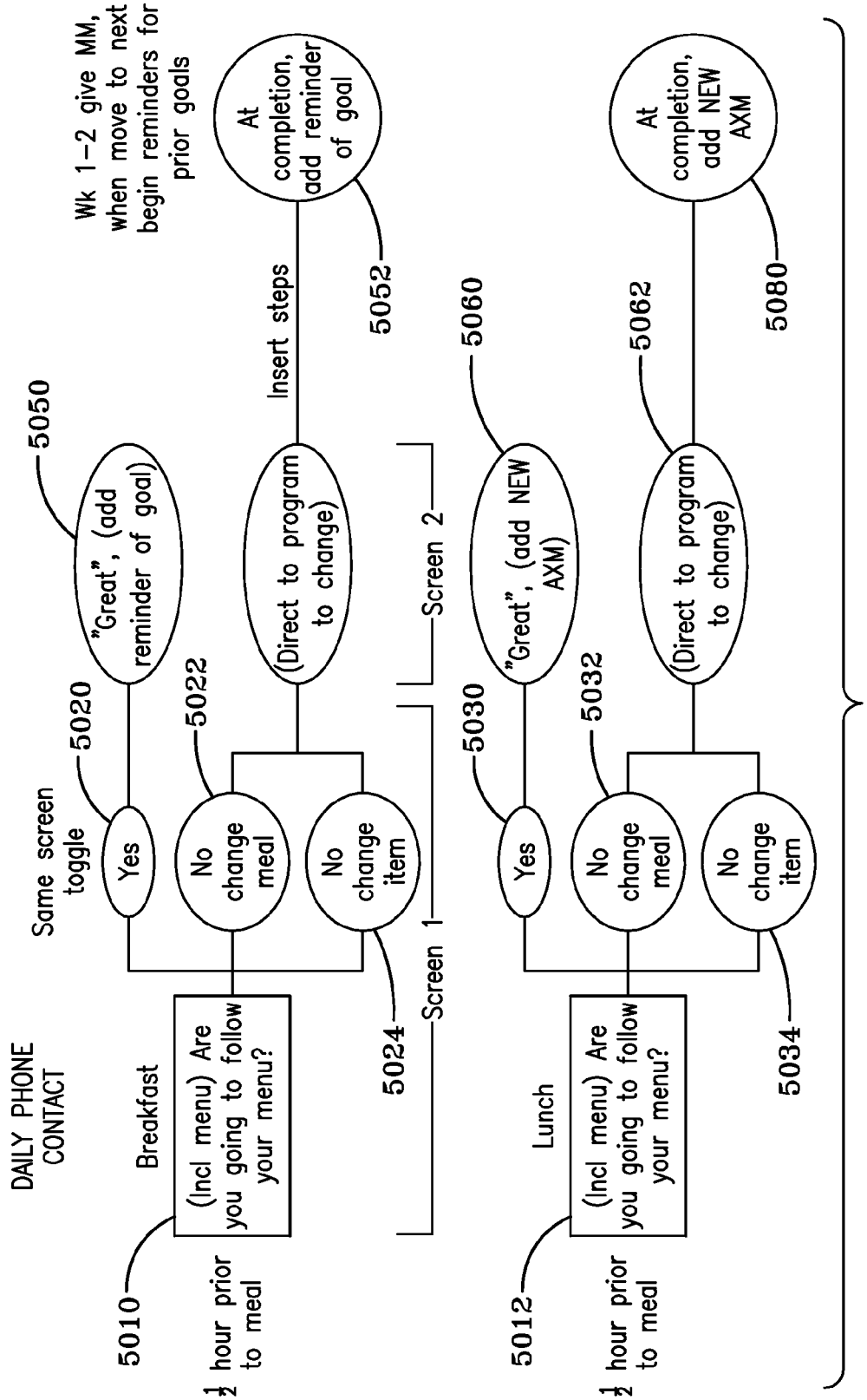
Figure 4C:
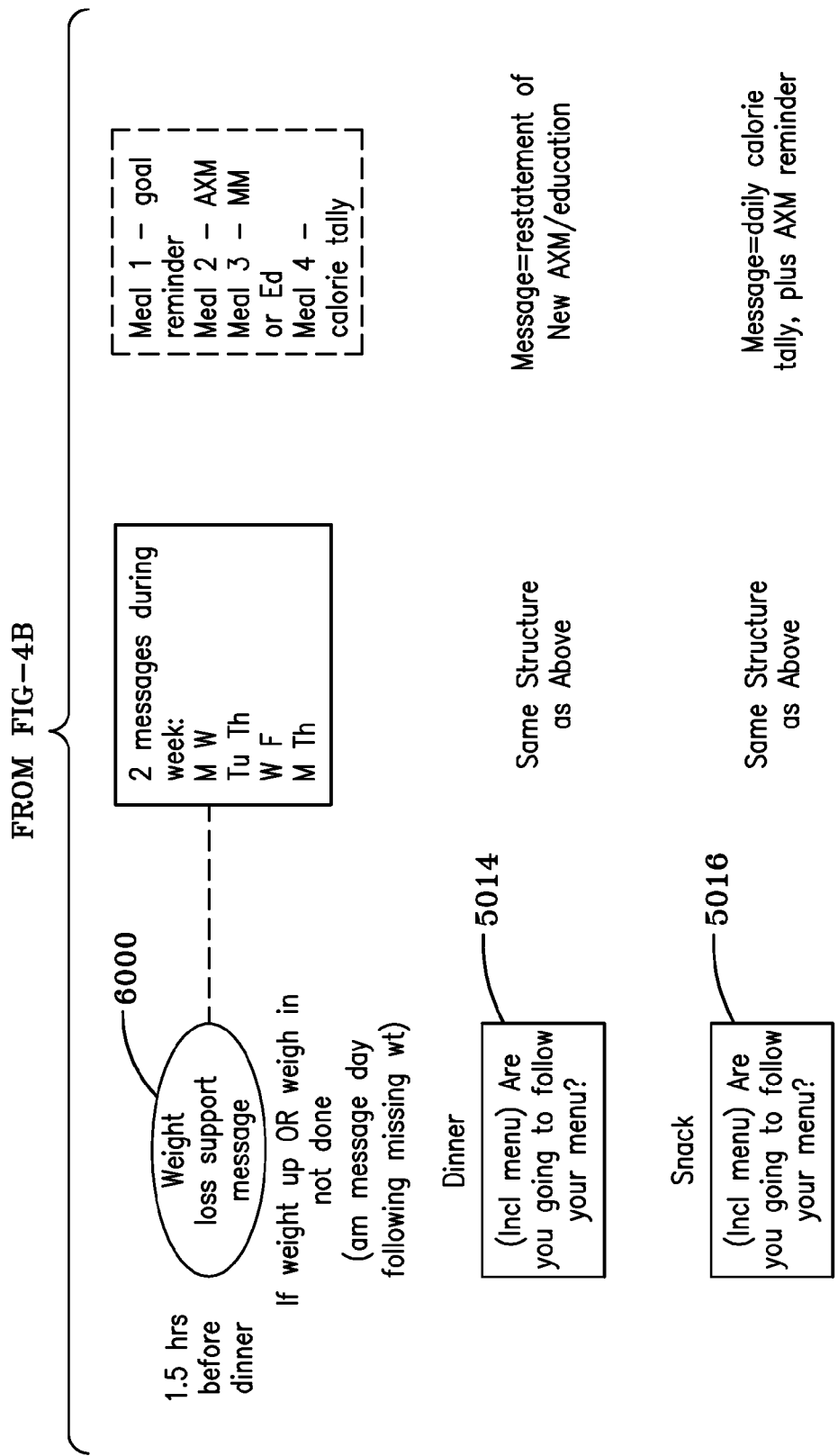

FIGS. 4A-4C illustrate meal contact logic according to an example embodiment. Referring to FIG. 4A, the user's specified preferences 5000 and enrollment weight 5002 filter into menu generation. The user's specified preferences 5000 (provided during enrollment) include an individual user's diet plan, food preferences, meal times, meal preparation selections, etc. The starting or enrollment weight 5002 is the weight entered by the user at enrollment when he or she starting using the system and method. Once the computer based expert system has generated menus for an individual user according to preferences, a weekly menu message 5004 is pushed to the user. Because of the size of the message, the weekly menu message is emailed from the computer based expert system to the individual user. It could also be delivered via a text message to an individual user's cell phone, etc. An individual user may also receive a weekly weight prompt message 5006 that reports the weight change since enrollment.

As shown in FIGS. 4B and 4C, the meal contact logic of the system and method uses daily phone contacts 5010 through 5016 that are sent to an individual user before he or she eats a meal. The daily phone contacts 5010 through 5016 are sent approximately thirty minutes before a scheduled meal. The daily contact message 5010, 5012 asks the user to indicate whether he or she is going to eat the suggested meal (e.g., from an earlier received weekly menu message). The responses include a "Yes" response 5020, 5030 indicating the user plans to eat the suggested meal, a "No change meal" response 5022, 5032 indicating the user would like an entirely different meal, or a "No change item" response 5024, 5034 indicating the user would like to substitute one or more items in the suggested meal. If the user selects either "no" response 5022, 5024, 5030, 5032, the expert system accesses a database of meal and menu substitutions and suggests either an entirely new meal or one or more food substitutions. The new suggestions conform to the user's food preferences as well as dietary needs for meeting the target goal. If the user selects yes 5020, 5030, changes a meal 5022, 5032, or changes an item 5024, 5034, a reminder of the goal is sent 5050, 5052, 5080.

The daily phone contacts 5010 through 5016 can be used to remind an individual user what foods he or she needs to be eating to reach the desired goal. In one embodiment, the computer based expert system has access to data concerning the location of an individual user (e.g., using a GPS feature on the user's mobile phone) and uses that information in generating appropriate meal daily phone contacts 5010 through 5016. For example, the computer based expert system may have data indicating an individual user works in downtown Chicago Monday through Thursday but works from home on Fridays. If the user has a dinner meal preparation preference for restaurant (ordered) food, on Mondays through Thursdays, the system generates daily phone contacts 5014 containing meal suggestions incorporating restaurants located near the user's office in downtown Chicago and similarly, on Fridays the system generates daily phone contacts 5014 with meal suggestions incorporating restaurants located near the user's home.

As shown in FIG. 4C a weight loss support message 6000 may be sent from the computer based expert system to an individual user. The message is sent twice a week, ninety minutes before dinner. A weight loss support message may remind the user of the week's progress toward the goal, provide the user with tips on what he or she might do to increase the likelihood of reaching the goal, etc.

Figure 5A:
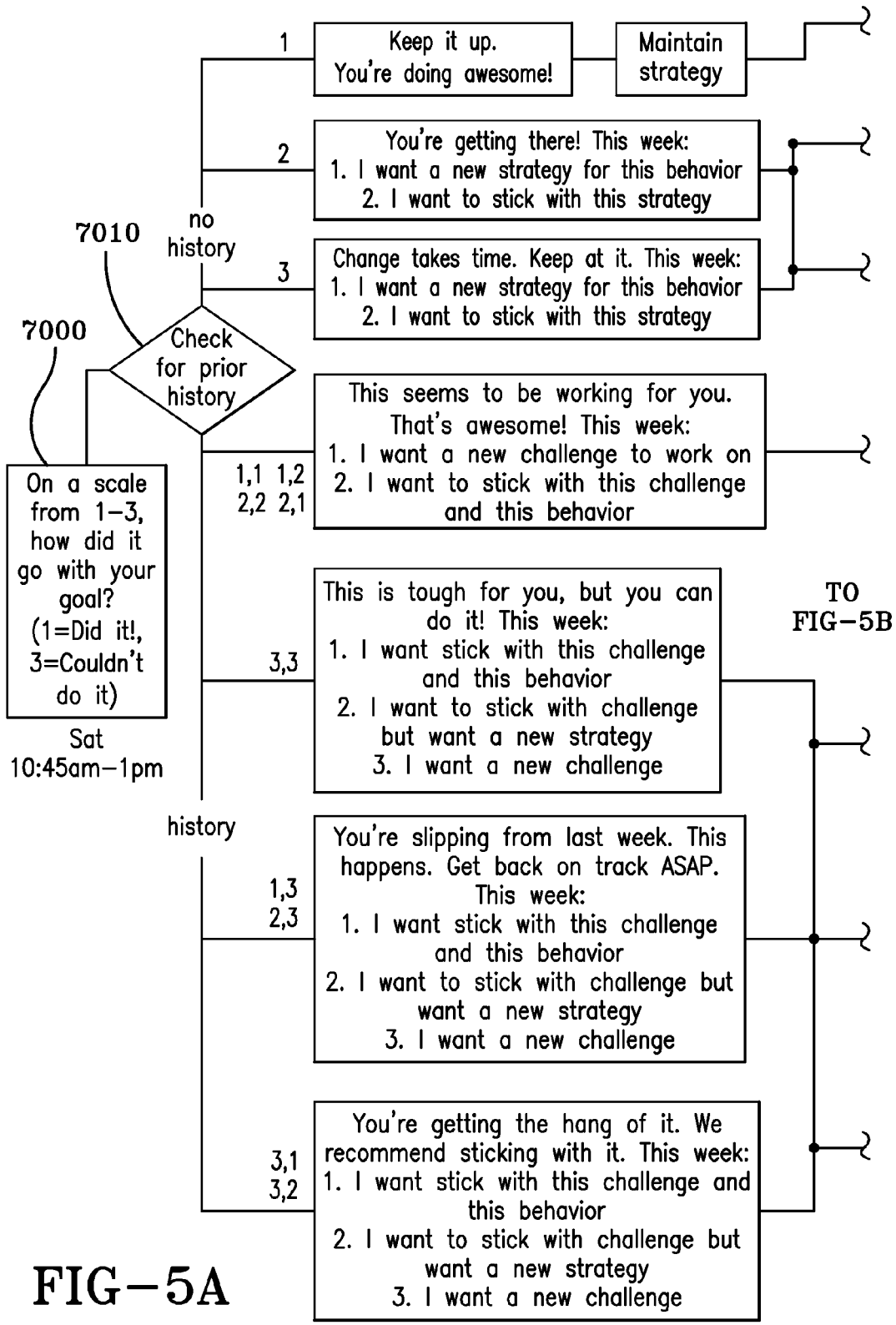
FIGS. 5A and 5B are a flowchart of tailored challenge messaging according to an example embodiment.
Figure 5B:
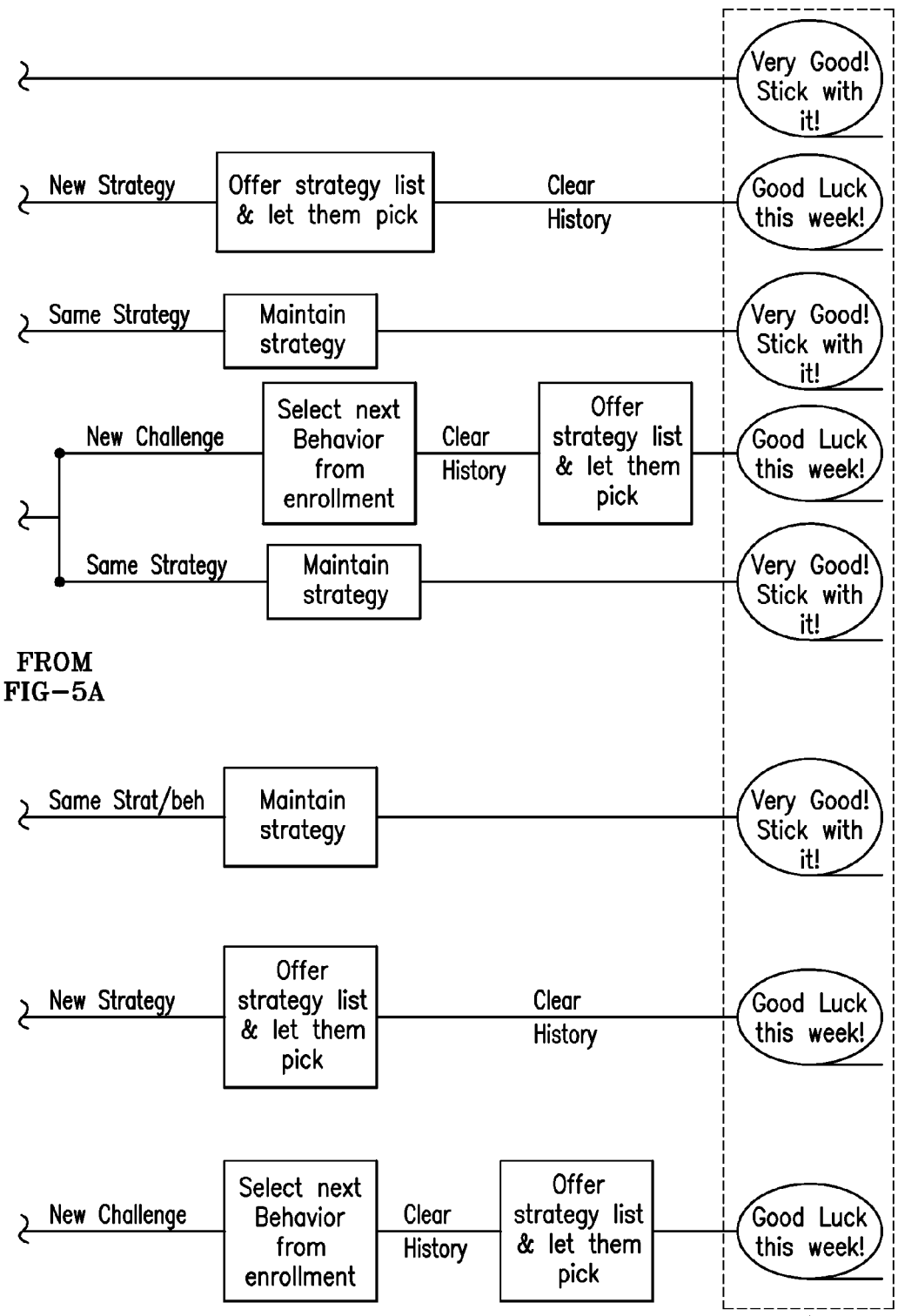

FIGS. 5A and 5B are a flowchart for tailored challenge messaging according to an example embodiment. After an individual user has been prompted to participate in a particular activity, the computer based expert system generates and sends a gauging message 7000. The gauging message 7000 asks the user to rate his or her experiencing in reaching a goal (e.g., 1=did it, 3=couldn't do it). The user response to a gauging message 7000 triggers a check for prior history function 7010 within the computer based expert system and causes it to analyze the user's latest response in comparison to previously entered responses in order to generate a variety of strategy suggestions 7020. The challenge suggestions range from telling the user to continue his or her efforts, offering a new strategy to an individual user who seems to be slipping, or identifying a new challenge. Follow up messages may be sent and differ based on whether the user is planning to continue working toward the current goal or to start working on a new strategy or challenge.

Figure 6A:
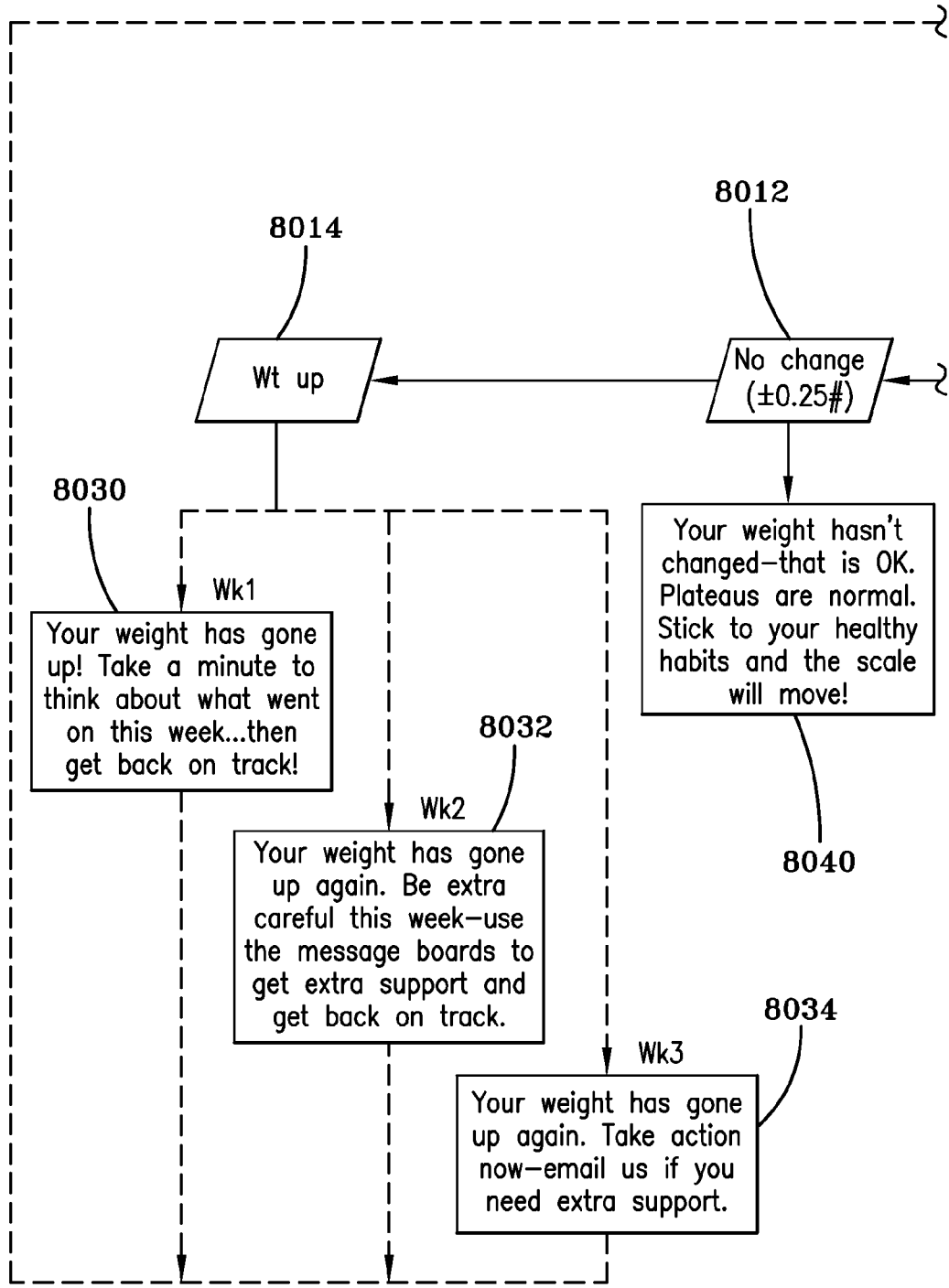
FIGS. 6A and 6B are a flowchart of tailored weight messaging according to an example embodiment.
Figure 6B:
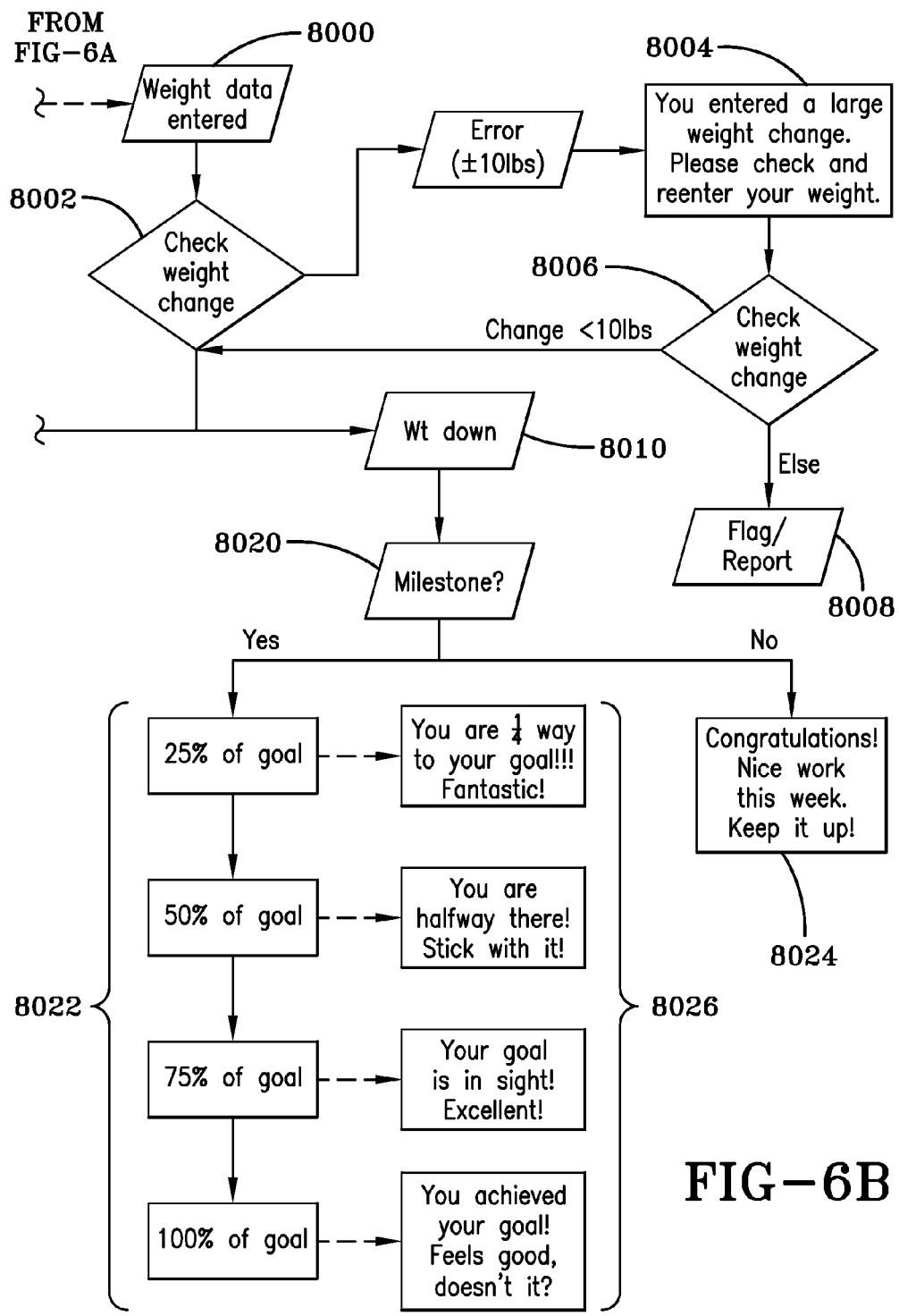

FIGS. 6A and 6B are a flowchart of tailored weight messaging according to an example embodiment. Referring to 6B, tailored messages may be generated for a user in response to the individual's entered weight data 8000. Once an individual user has entered weight data, the computer based expert system performs a weight change check 8002 and checks the individual's current weight against previously entered weight values. If a weight change check 8002 indicates that a user has lost or gained more than a specified number of pounds (e.g., 10), the computer based expert system generates a message 8004 indicating that there may have been a data entry error and prompts the user to check the entered weight value. The user reenters the weight value and if the weight change check 8006 indicates a weight loss or gain greater than the specified number of pounds a second time, it flags the entry and generates a report 8008.

If a weight change check 8002 or 8006 indicates a weight loss or gain of less than 10 pounds, the computer based expert system analyzes the individual user's current weight status in relation to the goal. If the user has lost weight, the computer based expert system performs a milestone determination 8020. For example, the computer based expert system may maintain four milestone values 8022 at 25%, 50%, 75%, and 100% of an individual user's goal and when the user's weight change check 8002 or 8006 indicates that one of the milestone values 8022 has been reached, a corresponding motivational message 8026 is sent to the user. If an individual has lost weight, but the weight loss does not result in the user reaching a milestone value 8022, a congratulatory message 8024 is sent to the user.

If a weight gain check 8002 or 8006 indicates a user has not lost or gained weight 8012, the computer based expert system can generate a consolation message 8040 reminding the user that plateaus are normal. If a weight gain check 8002 or 8006 indicates an individual user has gained weight 8014, the computer based expert system determines how many weigh-ins have indicated a weight gain for the individual user and generates a corresponding strategy message 8030 through 8034 to help the individual get back on track to reaching the goal weight.

Any embodiment may include any of the optional or preferred features of the other embodiments. The exemplary embodiments herein disclosed are not intended to be exhaustive or to unnecessarily limit the scope of the invention. The exemplary embodiments were chosen and described in order to explain the principles so that others skilled in the art may practice the invention. Having shown and described exemplary embodiments, those skilled in the art will realize that many variations and modifications may be made to affect the described invention. Many of those variations and modifications will provide the same result and fall within the spirit of the claimed invention. It is the intention, therefore, to limit the invention only as indicated by the scope of the claims.

What is claimed is:

1. A computerized system for personalizing and sending to portable device users tailored messages to promote modifications to dietary health behaviors, comprising:
    a first computerized database configured to store personal and diet preference data for a plurality of portable device users:
        (i) said personal data comprising contact data for sending messages to portable devices of said portable device users; and
        (ii) said diet preference data comprising at least one preferred meal time of day;
    a second computerized database configured to store dietary and nutritional data for a plurality of foods and recipes;
    a server executing programming instructions for:
        (a) analyzing diet preference data from said first computerized database for said plurality of users;
        (b) analyzing dietary and nutritional data from said second computerized database;
        (c) generating a tailored message for each of said plurality of users wherein said tailored message comprises:
            (i) a meal suggestion based on said analysis of diet preference data and dietary and nutritional data; and
            (ii) an acceptance option for said meal suggestion;
        (d) defining a time interval consisting of a plurality of minutes for scheduling message delivery times;
        (e) scheduling pre-determined times for delivering said tailored messages to said portable devices wherein said pre-determined times are within said time interval in advance of said preferred meal time of day specified by each of said plurality of users;

(f) sending from said server said tailored messages to said portable devices for delivery at said pre-determined times; and (g) receiving at said server from said portable devices responses to said acceptance option.

2. The computerized system of claim 1, wherein said portable devices of said plurality of portable device users are cellular telephones.

3. The computerized system of claim 1, wherein said time interval is between 15 to 45 minutes.

4. The computerized system of claim 1, wherein said acceptance option is selected from the group consisting of a response indicating acceptance of said meal suggestion and a response rejecting said meal suggestion.

5. The computerized system of claim 4, wherein said server further generates tailored messages comprising substitute meal suggestions for users rejecting said meal suggestions.

6. The computerized system of claim 5, wherein said substitute meal suggestion is a suggestion for substituting a single food item in said meal suggestion.

7. The computerized system of claim 1, wherein said dietary preference data comprises meal preparation preferences selected from the group consisting of meals prepared in under 10 minutes, meals prepared in over 10 minutes, frozen and ready to eat meals, fast food meals, and cooked to order meals.

8. The computerized system of claim 1 further comprising:
a third computerized database configured to store exercise data, said exercise data including data regarding calories burned for each of a plurality of exercises; and
exercise preference data for said plurality of users, said exercise preference data comprising physical activity preferences and exercise time of day preferences for performing said physical activity.

9. The computerized system of claim 8, wherein said server analyzes said exercise preference data for said plurality of users and generates a tailored exercise message for each of said users comprising a physical activity suggestion based on said exercise preference data and said exercise data, said tailored exercise message sent for delivery to said portable devices at pre-determined times within said time interval in advance of said exercise time of day preferences specified by each of said plurality of portable device users.

10. The computerized system of claim 1 wherein said server generates a personal strategy message for each of said users and said server sends said personal strategy messages for delivery to said portable devices, each of said personal strategy messages related to progress toward meeting a specified health behavior challenge.

11. A computerized method for personalizing messages from an expert system to modify health behavior comprising:
(a) receiving at a server from a user personal and preference data:
(i) said personal data comprising contact information for a portable device; and
(ii) said preference data comprising dietary and exercise preferences including a preferred time of day for completing activities related to said diet and exercise preferences;
(b) generating at said server for said user a tailored message comprising:
(i) an activity to be performed by said user consistent with said dietary and exercise preferences; and
(ii) an acceptance option for said activity;
(c) determining at said server said user's preferred time of day for starting said activity;

(d) defining at said server a time interval consisting of a plurality of minutes for scheduling message delivery times;
(e) scheduling at said server a pre-determined time to deliver said tailored message to said portable device wherein said pre-determined time is within said time interval in advance of said user's preferred time of day;
(f) sending said tailored message from said server to said portable device at said pre-determined time; and
(g) receiving at said server from said portable device a response to said acceptance option.

12. The computerized method of claim 11 wherein generating at said server a tailored message for an activity comprises generating a tailored message for eating a meal.

13. The computerized method of claim 12 wherein sending said tailored message from said server to said portable device at a pre-determined time within said time interval comprises sending said tailored message to said portable device 15 minutes before said user's preferred time for eating said meal.

14. The computerized method of claim 12 wherein generating at said server a tailored message for eating a meal comprises generating a tailored message with a meal suggestion consistent with said user's dietary preferences.

15. The computerized method of claim 14 wherein receiving at said server from said user an acceptance response to said meal suggestion comprises a rejection of said meal suggestion.

16. The computerized method of claim 15 further comprising sending from said server to said portable device for said user a substitute meal suggestion consistent with said user's dietary preferences.

17. The computerized method of claim 12 wherein sending said tailored message from said server to said portable device at a pre-determined time within said time interval comprises sending said tailored message to said portable device 15 minutes before said user's preferred time for starting said physical activity.

18. The computerized method of claim 11 wherein generating at said server a tailored message related to an activity comprises generating a tailored message for performing a physical activity.

19. The computerized method of claim 11 further comprising receiving at said server from said user data for a behavioral challenge.

20. The computerized method of claim 19 further comprising sending from said server to said portable device for said user a tailored message related to said behavioral challenge.

21. A computerized method for personalizing messages from an expert system to modify health behavior comprising:
(a) receiving at a server from a user:
(i) personal data comprising contact information for a portable device; and
(ii) preference data comprising health activity preferences;
(iii) a health goal;
(iv) selection of a health behavior challenge;
(v) selection of a challenge strategy;
(b) generating at said server and transmitting from said server to said portable device a tailored activity message comprising a health activity to be performed by said user consistent with:
(i) said health activity preferences; and
(ii) said health goal;
(c) generating at said server and transmitting from said server to said portable device a tailored gauging message comprising a request to rate performance of said health activity;

(d) receiving at said server said user response to said gauging message;

(e) generating at said server and transmitting from said server to said portable device a tailored strategy suggestion message consistent with:
  (i) said user selected health behavior challenge; and
  (ii) said user selected challenge strategy.

22. The computerized method of claim 21 wherein generating at said server and transmitting from said server to said portable device a tailored strategy suggestion message comprises generating a message selected from the group consisting of:
  (i) advising said user to continue current efforts;
  (ii) offering to said user a new strategy; and
  (iii) identifying for said user a new challenge.

23. The computerized method of claim 22 further comprising:
  (f) receiving at said server said user response to said tailored strategy suggestion message; and
  (g) generating at said server and transmitting from said server to said portable device at least one additional message responsive to said user response to said tailored strategy suggestion message.

24. The computerized method of claim 21 wherein generating at said server and transmitting from said server to said portable device a tailored strategy suggestion message comprises analyzing said user's latest response in comparison to previously entered responses.

25. The computerized method of claim 21 wherein said health activity is selected from the group consisting of an eating activity and an exercise activity.

* * * * *